(12) United States Patent
Altman et al.

(10) Patent No.: US 7,778,380 B2
(45) Date of Patent: Aug. 17, 2010

(54) DATA HANDLING AND ANALYSIS IN COMPUTED TOMOGRAPHY WITH MULTIPLE ENERGY WINDOWS

(75) Inventors: Amiaz Altman, Tel Aviv (IL); Galit Naveh, Haifa (IL); Raz Carmi, Haifa (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 221 days.

(21) Appl. No.: 12/065,611

(22) PCT Filed: Aug. 18, 2006

(86) PCT No.: PCT/IB2006/052867
§ 371 (c)(1),
(2), (4) Date: Mar. 4, 2008

(87) PCT Pub. No.: WO2007/029129
PCT Pub. Date: Mar. 15, 2007

(65) Prior Publication Data
US 2008/0226017 A1    Sep. 18, 2008

Related U.S. Application Data

(60) Provisional application No. 60/596,169, filed on Sep. 6, 2005.

(51) Int. Cl.
*A61B 6/00* (2006.01)
(52) U.S. Cl. .............................................. 378/4; 378/5
(58) Field of Classification Search ................... 378/4, 378/5
See application file for complete search history.

(56) References Cited

U.S. PATENT DOCUMENTS

| | | | |
|---|---|---|---|
| 2002/0081007 A1* | 6/2002 | Arakawa | 382/130 |
| 2003/0147502 A1 | 8/2003 | Heismann et al. | |
| 2004/0022359 A1 | 2/2004 | Acharya et al. | |
| 2004/0101086 A1* | 5/2004 | Sabol et al. | 378/4 |
| 2004/0102688 A1 | 5/2004 | Walker et al. | |
| 2004/0136491 A1 | 7/2004 | Iatrou et al. | |
| 2004/0184574 A1* | 9/2004 | Wu et al. | 378/5 |
| 2004/0199064 A1* | 10/2004 | Van Liere et al. | 600/407 |

(Continued)

FOREIGN PATENT DOCUMENTS

EP        1387320 A2    4/2004

(Continued)

OTHER PUBLICATIONS

Carmi, et al.; "Material Separation with Dual-Layer CT", Nuclear Science Symposium Conference Record, 2005 IEEE, Oct. 23, 2005-Oct. 29, 2005 pp. 1876-1878.

(Continued)

*Primary Examiner*—Edward J Glick
*Assistant Examiner*—Alexander H Taningco

(57) ABSTRACT

An apparatus includes a computed tomography (CT) scanner (10), a reconstructor (46), a polychromatic corrector (50), a material classifier (54) and an image processor (60). The scanner provides spectral CT information. The reconstructor (46) reconstructs the data from the CT scanner (10) into a volume space. The material classifier (54) determines a material composition of locations in the volume space as a function of their location in an attenuation space. Information indicative of the material composition is presented on a display (62).

24 Claims, 6 Drawing Sheets

U.S. PATENT DOCUMENTS

| | | | |
|---|---|---|---|
| 2004/0223585 | A1 | 11/2004 | Heismann et al. |
| 2004/0264626 | A1* | 12/2004 | Besson .......................... 378/4 |
| 2005/0002484 | A1* | 1/2005 | Wu et al. ....................... 378/4 |
| 2005/0084069 | A1 | 4/2005 | Du et al. |
| 2005/0135664 | A1* | 6/2005 | Kaufhold et al. ............ 382/131 |
| 2006/0109949 | A1* | 5/2006 | Tkaczyk et al. ................ 378/4 |

FOREIGN PATENT DOCUMENTS

| | | |
|---|---|---|
| WO | 2006114715 A2 | 11/2006 |
| WO | 2006121673 A1 | 11/2006 |

OTHER PUBLICATIONS

Zhang, et al.; "An H-L Curve Method for Material Discrimination of Dual Energy X-Ray Inspection Systems", Nuclear Science Symposium Conference Record, 2005 IEEE Oct. 23-29, 2005 pp. 326-328.

Ogorodnikov, S., et al.; "Processing of Interlaced Images in 4-10 MeV Dual Energy Customs System for Material Recognition," Physical Review Special Topics-Accelerators and Beams, ID. 104701, The American Physical Society, 5 (10) pp. 1-11, 2002.

Alvarez, et al.; "Energy-Selective Reconstruction in X-Ray Computerized Tomography," Phys. Med. Biol., 1976, 21(5), pp. 733-744, Dept. of Electrical Engineering, Stanford University, Stanford, CA.

Kalender, et al.; Evaluation of a Prototype Dual-Energy Computed Tomographic Apparatus, I. Phantom Studies, May/Jun. 1986, 13(3), pp. 334-339, Am Assoc. Phys. Med.

Vetter, et al.; "Evaluation of a Prototype Dual-Energy Computed Tomographic Apparatus, II. Determination of Vertebral Bone Mineral Content," May/Jun. 1986, 13(3) pp. 340-343, Am. Assoc. Phys. Med.

Goh, et al.; "Energy-Dep[endent Systematic Errors in Dual-Energy X-Ray CT," IEEE Transactions on Nuclear Science, Apr. 1997, 44(2), pp. 212-217.

Goh, et al.; "Correction of Energy-Dependent Systematic Errors in Dual-Energy X-Ray CT using a Basis Material Coefficients Transformation Method," IEEE Transactions on Nuclear Science, Dec. 1997, 44(6) pp. 2419-2424.

Hassler, et al.; "X-Ray Dual-Energy Calibration Based on Estimated Spectral Properties of the Experimental System," IEEE Transaction on Nuclear Science, Jun. 1998, 45(3) pp. 1699-1712.

Walter, et al.; "Dual kVp Material Decomposition Using Flat-Panel Detectors," Proceedings of SPIE, 2004, vol. 5368 pp. 29-39, Physics of Medical Imaging.

Heismann, et al.; "Technology and Image Results of a Spectral CT System," Proceedings of SPIE, 2004, vol. 5368, pp. 52-59, Physics of Medical Imaging.

* cited by examiner

DATA HANDLING AND ANALYSIS IN COMPUTED TOMOGRAPHY WITH MULTIPLE ENERGY WINDOWS

CROSS REFERENCE TO RELATED APPLICATIONS

This application claims the benefit of U.S. provisional application Ser. No. 60/596,169 filed Sep. 6, 2005, which is incorporated herein by reference.

The present invention relates to the analysis of data generated by x-ray computed tomography (CT) and other systems which provide spectral information, and more particularly to determining the material composition of an object examined using such a system. It finds particular application in medical imaging, and also has application in non-destructive testing and analysis, security applications, and other applications where material decomposition abilities are useful.

Computed tomography (CT) scanners generate images indicative of the x-ray attenuation of an object under examination. The x-ray tubes employed in CT scanners typically produce x-rays having a single, relatively wide energy spectrum. Similarly, the detectors employed in such systems typically provide limited, if any, information about the energy spectrum of the detected radiation. While these scanners provide valuable information about the internal structure of an object under examination, they have limited ability to provide information about the material composition of the object, especially where different compounds have similar radiation attenuations.

The ability to determine the material composition of an object under examination can have various applications. In the medical field, these include the analysis and classification of coronary artery calcification and soft plaque, the analysis and segmentation of neck and head arteries (differentiating between bone and vessel), analyzing and segmenting peripheral artery disease, general enhancement of the contrast between an iodine filled lumen and the vessel wall, quantification in perfusion studies, multi-tissue differentiation and analysis in virtually all body parts, and imaging of small amounts of heavy materials as molecular functional imaging tracers.

Because different compounds can change the attenuated radiation spectrum in different ways, dual-energy scanning has been suggested as a technique for improving material separation capabilities. The idea is to scan with two or more different x-ray spectra or to acquire data using detectors which provide spectral information. See *Evaluation of a Prototype Dual-Energy Computed Tomographic Apparatus, I. Phantom Studies*, by W. A. Kalender, et al., Phys. 13 (3), pp. 334-339 (1986); *Evaluation of a Prototype Dual-Energy Computed Tomographic Apparatus, II. Determination of vertebral bone mineral content*, by J. R. Vetter, et al., Phys. 13 (3), pp 340-343 (1986); *Technology and image results of a spectral CT system*, B. J. Heismann, et al., SPIE proceedings Vol. 5368 (May, 2004), pp. 52-59; and *Dual Kvp Material Decomposition Using Flat-Panel Detectors*, D. Walter, et al., SPIE proceedings Vol. 5368 (May, 2004), pp. 29-39.

One technique for obtaining data having multiple energy channels or windows is to switch the x-ray tube voltage between multiple values (e.g. 140 kv and 80 kv) in successive frames. Another technique is to provide a radiation filter after the x-ray tube, where the filter is alternated between successive frames. Another technique uses multi-energy detectors; still another uses photon counting detectors. See US Published Patent Application No. 20040022359 entitled *Method, System and Computer Product for Plaque Characterization*, Acharya, et al.; US Published Patent Application No. 20040136491 entitled *Methods and Systems for Detecting Components of Plaque*, Iatrou, et al.

One strategy for processing dual energy CT data has been to perform material decomposition on the projection measurements before the reconstruction step. A second has been to perform post-processing manipulations on the images reconstructed from each of the energy windows. See *Energy-selective Reconstruction in X-ray Computerized Tomography* by R. E. Alvarez and A. Macovski, Phys. Med. Biol. 21, 733 (1976).

The first strategy has usually been based on decomposition into two base materials (e.g. soft tissue and bone). In theory, it can be shown that scanning with two energy windows is sufficient to express all materials as linear combinations of two known selected materials. However, the analysis of data at the pre-reconstruction stage is more complicated and is not necessarily robust if many different materials appear in the scanned object. Moreover, the theoretical model usually used in this analysis is not accurate if material in the scanned object has an absorption edge in or near the relevant energy windows (such as Iodine, with a K-edge at about 33 kev).

The post-processing strategy usually involves a third image created by subtracting the images generated from the two energy windows. This difference image has been used to create some enhancement or material decomposition equivalent, for example by using additional special calibrations. See US Published Patent Application No. 20040022359 entitled *Method, System and Computer Product for Plaque Characterization*, Acharya, et al.; US Published Patent Application No. 20040136491 entitled *Methods and Systems for Detecting Components of Plaque*, Iatrou, et al.

While the post-processing technique is usually simpler and more robust then the pre-processing analysis, it may be more sensitive to beam-hardening effect. In addition, the subtraction of the images of the two energy windows does not necessary give the optimal solution.

Aspects of the present invention address these matters, and others.

According to one aspect of the invention, a method includes receiving first data indicative of the radiation attenuation of a location in a volume space at a first energy spectrum receiving second data indicative of the radiation attenuation of the location in the volume space at a second energy spectrum, determining a material composition of the location in the volume space as a function of its location in an attenuation space, and generating an image indicative of the material composition. The step of receiving first data, receiving second data, and classifying is repeated for a plurality of locations.

According to a limited aspect of the invention, the method includes performing a first polychromatic correction based on the radiation attenuations of a plurality of locations in the volume space at the first energy spectrum and performing a second polychromatic correction based on the radiation attenuations of a plurality of locations in the volume space at the second energy spectrum. The polychromatic correction generates a first corrected radiation attenuation of the location in the volume space at the first energy spectrum and the polychromatic correction generates a second corrected radiation attenuation of the location in the volume space at the second energy spectrum. The step of receiving first data includes receiving the first corrected radiation attenuation and the step of receiving second data includes receiving the second corrected radiation attenuation.

According to a more limited aspect of the invention, the step of performing a first polychromatic correction includes generating a first attenuation map. The step of performing a second polychromatic correction includes generating a second attenuation map.

According to a limited aspect of the invention, the step of determining includes classifying the location as containing one of at least first and second materials.

According to a more limited aspect of the invention, one of the materials is a mixture of materials, or an indeterminate material. The method may also include classifying the location as containing one of at least bone and contrast material.

According to a limited aspect of the invention, the step of generating an image includes generating image data for a plurality of locations in the volume space according to the function $P_l = f(\mu l, Ml)$ where the P is the image data, $\mu$ is a radiation attenuation, M is the material composition, and l is the location in the volume space.

According to a more limited aspect of the invention, the radiation attenuation $\mu$ is a composite of the radiation attenuation at the first energy spectrum and the radiation attenuation at the second energy spectrum.

According to a limited aspect of the invention, the step of generating includes generating an image which includes the radiation attenuation of a plurality of locations in the volume space with the material composition superimposed thereon.

According to a limited aspect of the invention, the method includes receiving computed tomography scan data indicative of the radiation attenuation along a plurality of projections through an object at the first energy spectrum, receiving computed tomography scan data indicative of the radiation attenuation along a plurality of projections through the object at the second energy spectrum, reconstructing the scan data from the first energy to generate data indicative of the radiation attenuation of the object at a plurality of locations in the volume space at the first energy spectrum, and reconstructing the scan data from the second energy to generate data indicative of the radiation attenuation of the object at a plurality of locations in the volume space at the second energy spectrum.

According to another limited aspect of the invention, the step of determining includes determining the material composition according to the function $Ml = f(\mu 1l, \mu 2l)$, where M is the material composition, $\mu 1$ is the radiation attenuation at the first energy spectrum, $\mu 2$ is the radiation attenuation at the second energy spectrum, and l is the location in the volume space.

According to yet another limited aspect of the invention, the volume space is two dimensional.

According to still another limited aspect of the invention, the first and second energy spectra overlap.

According to another aspect of the invention, a method includes classifying a plurality of locations in a computed tomography image space according to a material classification function $Ml = f(\mu 1l, \mu 2l \ldots \mu n_l)$, where M is a material, n is the number of energy spectra, $\mu n$ is a radiation attenuation at energy spectrum n, and l is a location in the image space, and presenting a result of the classification in human readable form. N is greater than or equal to 2.

According to a limited aspect of the invention, the step of classifying a plurality of locations in the computed tomography image space includes classifying each location in the image space as a function of its location in an n-dimensional attenuation space.

According to another limited aspect of the invention, the method includes performing a polychromatic correction on the plurality of locations in the image space to generate a corrected radiation attenuation at each energy spectrum and using the corrected radiation attenuation to classify the plurality of locations.

According to a more limited aspect of the invention, performing a polychromatic correction includes generating an attenuation map for each energy spectrum n.

According to another limited aspect of the invention, presenting a result of the classification includes generating image data for the plurality of locations according to the function $P_l = f(\mu_l, M_l)$, where the P is the image data, $\mu$ is a radiation attenuation and M is the material.

According to a more limited aspect of the invention, the method includes generating an image which includes the radiation attenuation with the results of the classification superimposed thereon.

According to yet another limited aspect of the invention, $\mu_1$ is an attenuation based on a count of detected photons and $\mu_2$ is an attenuation based on an integral of the energies of detected photons.

Still other aspects of the present invention will be appreciated by those skilled in the art upon reading the appended description.

FIG. 1 depicts a computed tomography scanner and data processing.

FIG. 2 describes steps in establishing a material classification function.

Figure 1:
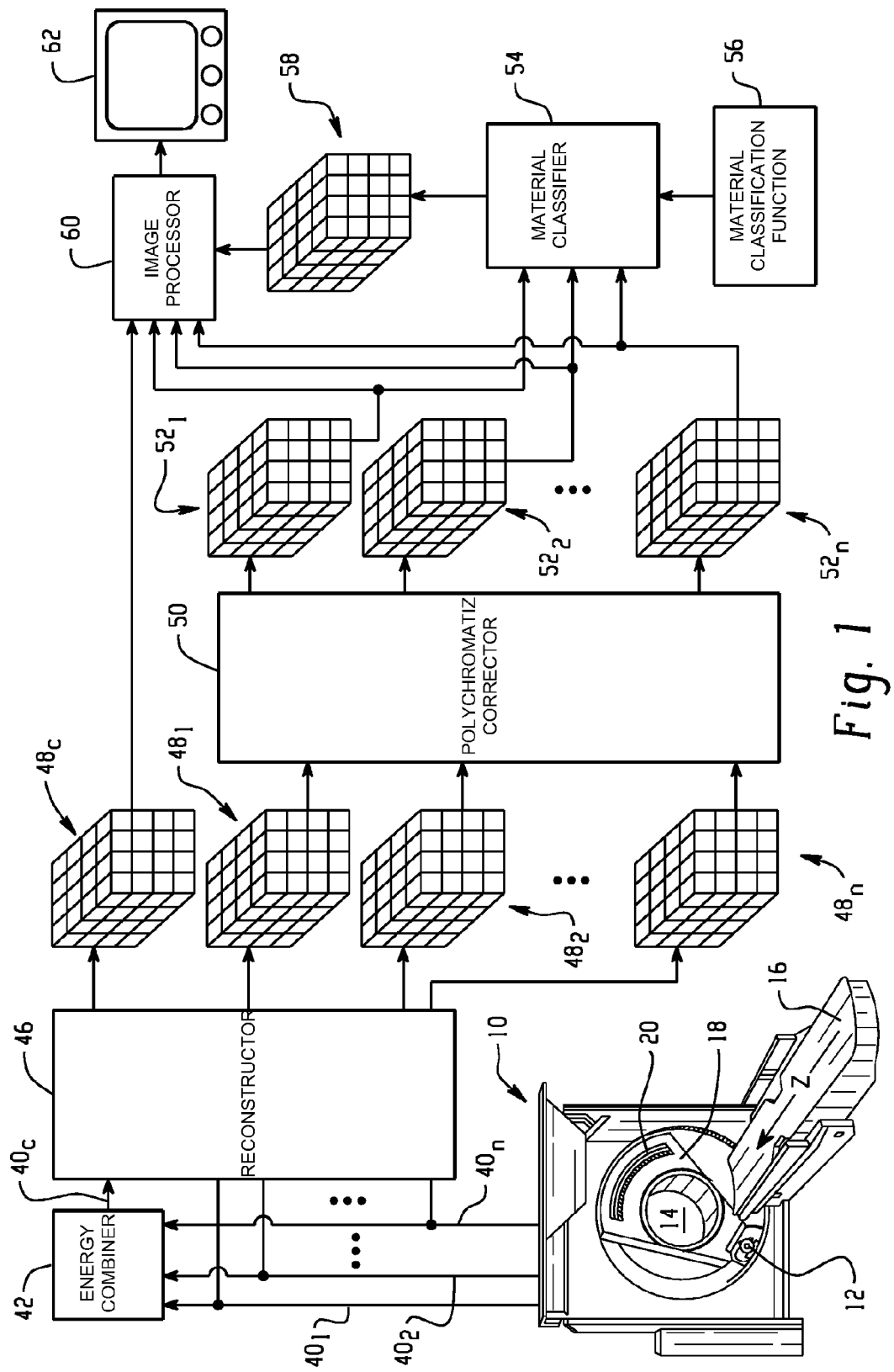

With reference to FIG. 1, a computed tomography (CT) scanner 10 provides CT data $40_1$, $40_2$ . . . $40_n$ for each of a plurality of energy spectra E1, E2 . . . En.

An exemplary scanner 10 includes a rotating gantry 18 which rotates about an examination region 14. The gantry 18 supports an x-ray source 12 such as an x-ray tube. The gantry 18 also supports an x-ray sensitive detector 20 which subtends an angular arc on the opposite side of the examination region 14. X-rays produced by the x-ray source 12 traverse the examination region 14 and are detected by the detector 20. Accordingly, the scanner 10 generates scan data indicative of the radiation attenuation along a plurality of projections through an object disposed in the examination region.

A support 16 such as a couch supports a patient or other object in the examination region 14. The patient support 16 is preferably movable in the z-direction. In a helical scan, movement of the support 16 and the gantry 18 are coordinated along with such that the x-ray source 12 and the detectors 20 traverse a generally helical path with respect to the patient.

In the case of a multi-slice scanner, the detector 20 includes two or more rows of detectors extending in the z-direction. Depending on the configuration of the scanner 10 and the detectors 20, the x-ray source 12 generates a generally fan, wedge, or cone shaped radiation beam. Moreover, a so-called fourth generation scanner configuration, in which the detector 20 spans an arc of 360 degrees and remains stationary while the x-ray source 12 rotates, may also be implemented.

In one embodiment, the detector 20 includes a multiple layer detector such as the detector disclosed in *Improved Detector Array for Spectral CT*, Levene et al., U.S. Application Ser. No. 60/674,905 filed Apr. 26, 2005, the contents of which are expressly incorporated by reference herein. The detector 20 provides scan data for each of two energy spectra $E_1$, $E_2$. Assuming an x-ray tube voltage of 140 kv, the two energy spectra would be roughly centered at 70 kev and 90 kev.

While improved material separation is generally achieved by increasing the spacing between the energy spectra $E_1$, $E_2 \ldots E_n$, reducing the width of the spectra, and reducing the overlap therebetween, those skilled in the art will recognize that these are not the only factors affecting overall system performance. Accordingly, the configuration of the CT scanner 10 of a particular situation, as well as the choice of technique(s) used to obtain the spectral information, (e.g. varying the source voltage, filtering, multi-energy detectors, photon counting detectors, or the like) may be influenced by and ultimately selected as a result of, a number of factors.

With continuing reference to FIG. 1, an energy combiner 42 receives the CT scan data $40_1, 40_2 \ldots 40_n$ and generates composite CT data $40_c$ analogous to the data acquired in conventional CT scan. The energy combiner 42 preferably combines the detector output signals prior to the log operation to generate a combined output signal. In a two energy system, the combined normalized output signal is generated according to the relation:

$$S_{combined} / S_{0combined} = \frac{(S_1/S_{01}) + (S_2/S_{02}) \cdot k}{1+k} \qquad \text{Eq. 1}$$

Where $S_1$ and $S_2$ are the signals at each energy, $S_{01}$ and $S_{02}$ are the signals as they are measured in air, and k is a constant for each detector pixel. Operation of the energy combiner, and particularly the determination of the constant k, is further described below.

Alternatively, the signals may be summed:

$$S_{combined} = S_1 + S_2 \qquad \text{Eq. 2}$$

The energy combiner 42 may also be omitted, for example where the spectral information is obtained by varying the voltage of the x-ray source or where, a composite CT data $40c$ is not needed.

A reconstructor 46 receives the CT scan data $40_1, 40_2 \ldots 40_n$ and the composite CT scan data $40_c$ and generates volumetric data $48_1, 48_2 \ldots 48_n$ indicative of the attenuation or radiodensity of the object under examination at each energy spectrum $E_1, E_2 \ldots E_n$ as well as composite volumetric data $48_c$ based on the composite data $40_c$. While the reconstructor 46 is depicted as a single reconstructor 46, the reconstructor 46 may include multiple reconstruction units such that the data $40_1, 40_2 \ldots 40_n$ are each reconstructed in parallel.

Exemplary reconstruction techniques include filtered backprojection and iterative techniques. Depending on the geometry of the detectors, the reconstruction may be based on two dimensional or volume based techniques. Suitable calibrations and corrections, such as a pre-processing polychromatic correction to correct the attenuation of water, are also applied. Similarly, iterative bone correction may also be employed to correct for beam-hardening in the presence of bones. In any case, various reconstruction techniques and systems are known in the art and the choice of technique for a particular system and application is influenced by a number of factors known to those skilled in the art.

The volumetric data $48_1, 48_2 \ldots 48_n$ and $48_c$ provides information in an image or volume space. More particularly, the volumetric data $48_1, 48_2 \ldots 48_n$ and the composite volumetric data $48_c$ can each be modeled as containing a plurality of voxels or pixels, each having a coordinate x, y, z in the volume space. The volumetric data may also provide information on only a single image slice, in which case the volume space may be modeled as a two dimensional space. The radiation attenuation at a given energy spectrum and location in volume space can be expressed as:

$$\mu n_{x,y,z} \qquad \text{Eq. 3}$$

where $\mu$ is the attenuation, n is the energy spectrum E, and x,y,z is the location. In CT, radiation attenuation is typically expressed in Hounsfield units (HU).

To correct for beam hardening, a polychromatic corrector 50 applies a polychromatic correction to the volumetric data $48_1, 48_2 \ldots 48_n$ to generate corrected volumetric data $52_1, 52_2 \ldots 52_n$. The polychromatic correction is further described below.

A material classifier 54 receives the corrected volumetric data $52_1, 52_2 \ldots 52_n$ and generates classified volume data 58. The classifier applies a material classification function 56 of the form:

$$M_{x,y,z} = f(\mu 1_{x,y,z}, \mu 2_{x,y,z} \ldots \mu n_{x,y,z}) \qquad \text{Eq. 4}$$

where M is a material composition. In the case of a system having data for two energies (i.e., n=2), the material classification function 56 can be expressed as:

$$M_{x,y,z} = f(\mu 1_{x,y,z}, \mu 2_{x,y,z}) \qquad \text{Eq. 5}$$

The material classification function is further described below.

An image processor 60 processes the composite volume data $48_c$ and the classified volume data 58 for presentation in human readable form on an output device 62 such as a monitor, display, or hardcopy output device. More particularly, the image processor 60 generates one or more images indicative of the material composition. The image processor 60 generates image data for a plurality of locations in the volume space according to the function:

$$P_{x,y,z} = f(\mu_{x,y,z}, M_{x,y,z}) \qquad \text{Eq. 6}$$

where P is the image data and $\mu$ is a radiation attenuation and M is the material. In one embodiment, the radiation attenuation is the composite attenuation $\mu c$. Alternatively, the radiation attenuation is the radiation attenuation at one of the other energies, or a combination thereof. Where the spectral information is obtained by varying the x-ray source voltage, the radiation attenuation at the higher of the tube voltages may be used. As the higher tube voltage tends to produce an x-ray beam having a relatively broader energy spectrum, the attenuation measured at the higher voltage provides a good indication of the radiation attenuation across a spectrum of energies.

With one technique for presenting the data is to assign a different color to each of the materials and to present a combined image with the respective colors overlaid on a gray scale image of the composite volume data $48_c$. Moreover, the color, opacity, or hue may be presented as a function of the confidence or probability that a particular location is a particular material. The color, opacity, or hue may be presented as a function of the material concentration. It may also be desirable to display only a single material or a subset of materials.

It may also be desirable to allow the user to vary the opacity of the enhancement colors on the grey-scale image, for example from completely transparent (0% opacity) to completely colored (100% opacity). The operator interface includes a slider or scroll bar which allows the user to adjust the opacity of the enhancement colors. Additional sliders allow the user to adjust the center and width of the HU window, respectively.

In addition, each of the data 58, 48$_1$, 48$_2$ ... 48$n$ and 48$_c$ may be presented separately, or they may be displayed in various combinations. If a composite image is not available, the classified volume data 58 can be used to enhance the attenuation data from one of the other energy ranges 48$_1$, 48$_2$ ... 48$_n$. As described below in connection with polychromatic correction, it is generally preferable to display the uncorrected data 48. However, the corrected data 52 may also be displayed.

Figure 8:
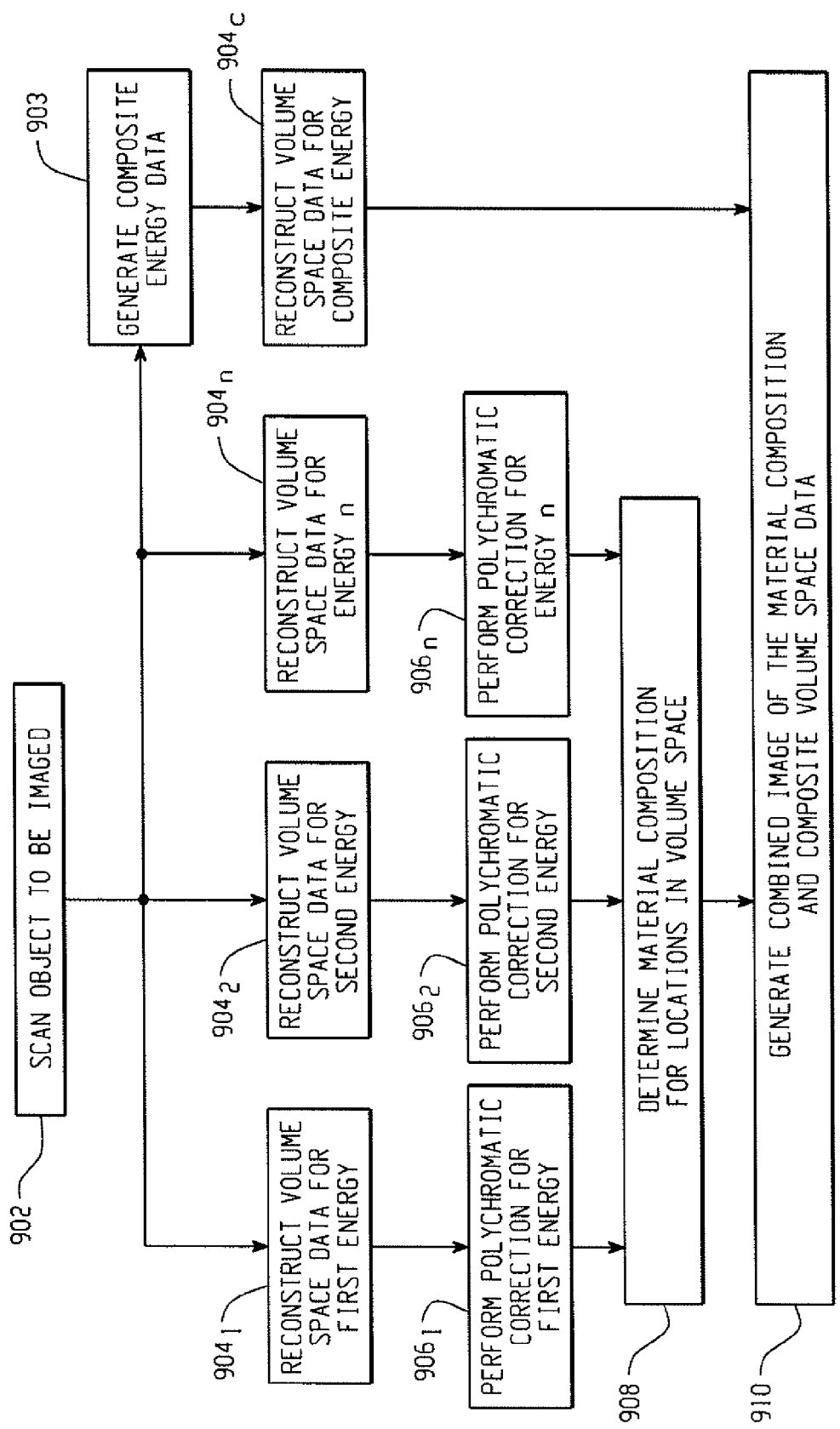
FIG. 8 depicts steps in determining a material classification.

In operation according to one embodiment of the invention, and with reference to FIG. 8, an object to be imaged is scanned at 902 to generate CT scan data for each of a plurality n of energy spectra. At 903, the CT scan data from the various energies is combined to generate composite CT data. At 904, the CT scan data for each energy and the composite data are reconstructed to generate volume space attenuation data for each energy. At 906, polychromatic correction is applied to the volume space attenuation data to create corrected volume space attenuation data for each energy. At 908, the material composition of each of the locations in the volume space is determined. At 910, an image including the material composition and the composite volume space data is generated and displayed.

The generation of the material classification function 56 will now be described in greater detail in connection with a scanner 10 which generates CT data 40$_1$, 40$_2$ for each of two energy spectra. The material classification function 56 may be determined once as an initial characterization of a particular configuration or family of scanners. In fact, information obtained while evaluating the material classification function may be used during the design process to optimize the design of the scanner 10, for example as an aid to selecting suitable detector materials or configurations, x-ray source energies, filters, or other techniques for obtaining both spectral or non-spectral data. If desired, the classification function 56 may also be determined or adjusted as a step during the production of a particular scanner or group of scanners. It may also be checked and updated from time to time over the life of the scanner 10, or even immediately preceding a particular imaging scan. As will be appreciated, and depending on the purposes for which the classification function 56 is being determined, some or all of the process may be carried out on different computers or processors, or even on a different scanner.

Figure 2:
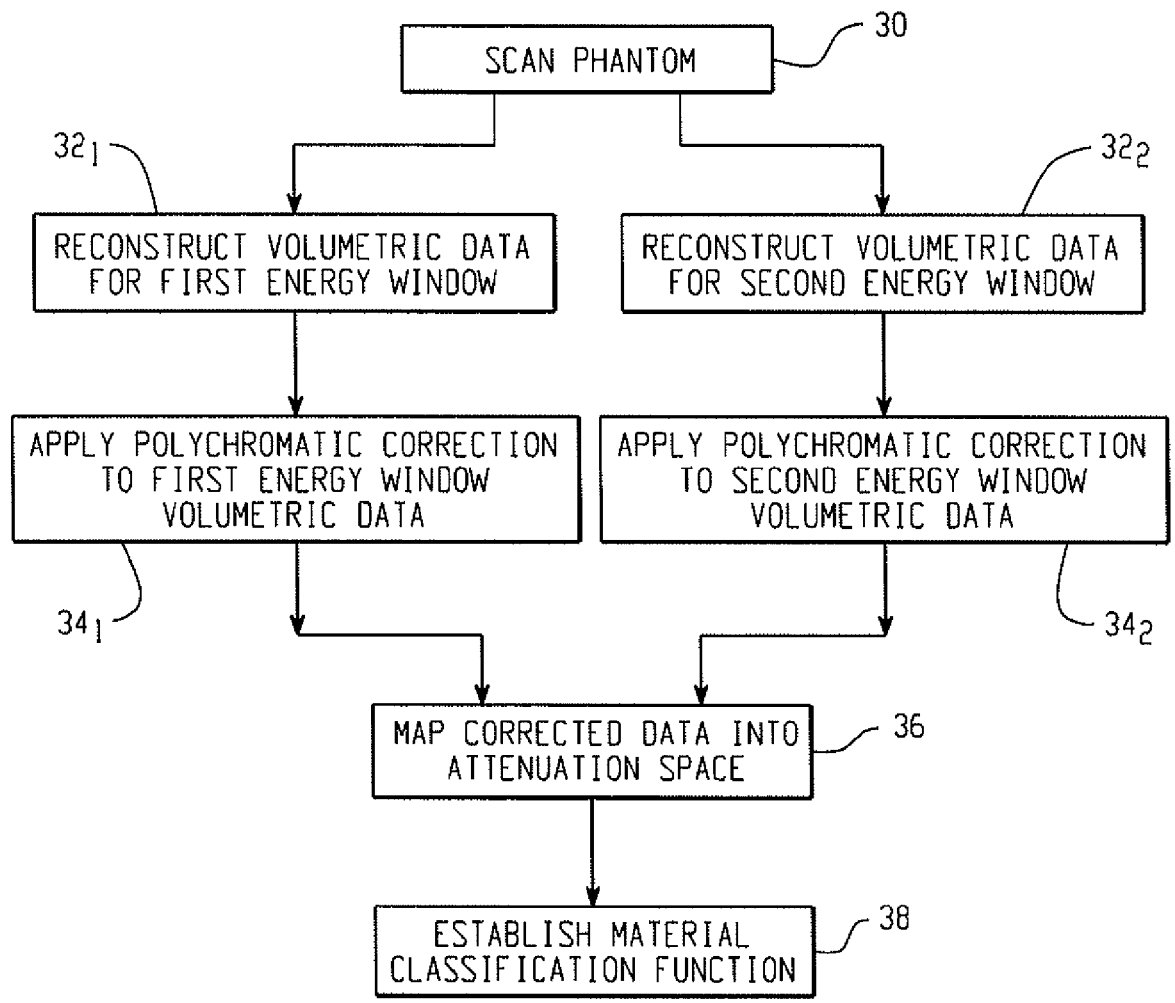
Figure 3:
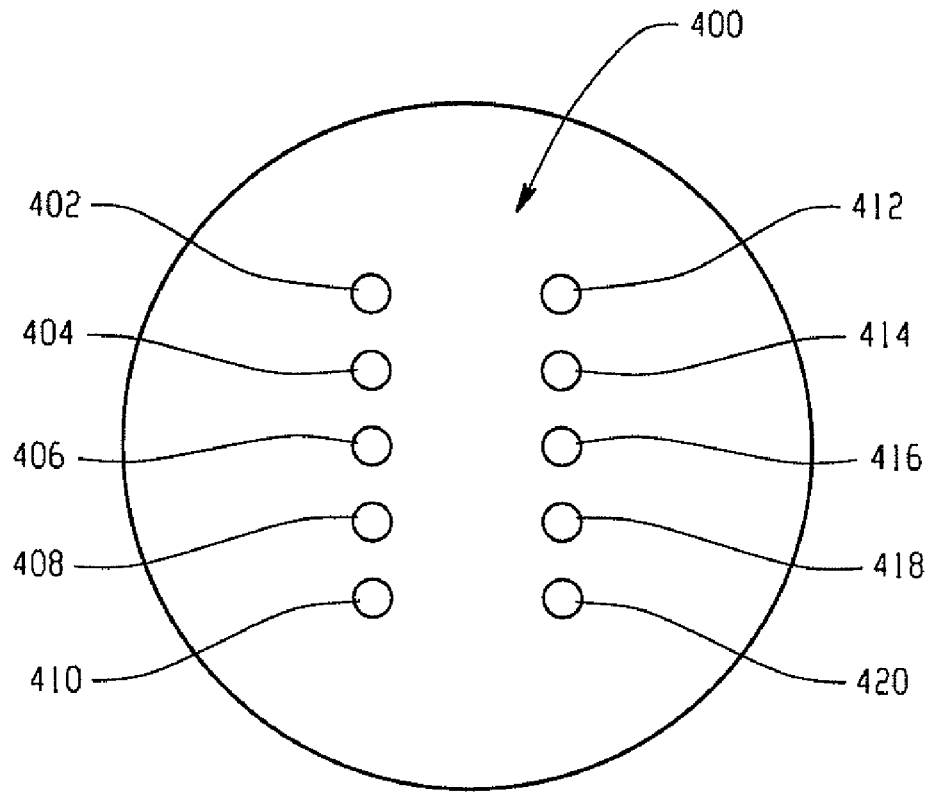
FIG. 3 is an end view of a generally cylindrical phantom.

With reference to FIGS. 2 and 3, a known phantom 400 is scanned at 30. A phantom 400 particularly well suited to classifying bone and contrast material is a 20 cm water cylinder containing ten 8 mm sample cylinders 402, 404, 406, 408, 410, 412, 414, 416, 418, 420. The sample cylinders 402, 404, 406, 408, 410 each contain a different iodine concentration, ranging from the highest at 402 to the lowest at 410. The sample cylinders 412, 414, 416, 418, 420 each contain a different calcium concentration, ranging from the highest at 412 to the lowest at 420. The concentrations in cylinders 404, 406, 414, and 416 are advantageously selected to be representative of concentrations typically encountered during scanning of the coronary arteries. Of course, different or additional materials, concentrations, numbers of sample cylinders, and relative physical locations of the cylinders may be implemented.

Returning to FIG. 2, at 32, and 322, the scan data 40 is reconstructed to generate volumetric data 48$_1$, 48$_2$ for each energy spectrum E$_1$, E$_2$. A polychromatic correction may be applied at 34$_1$ and 34$_2$ to generate corrected volumetric data 52$_1$ and 52$_2$ for each energy spectrum E$_1$, E$_2$ to correct for beam hardening in the phantom. Depending on the characteristics of the phantom, this step may be omitted.

Figure 4:
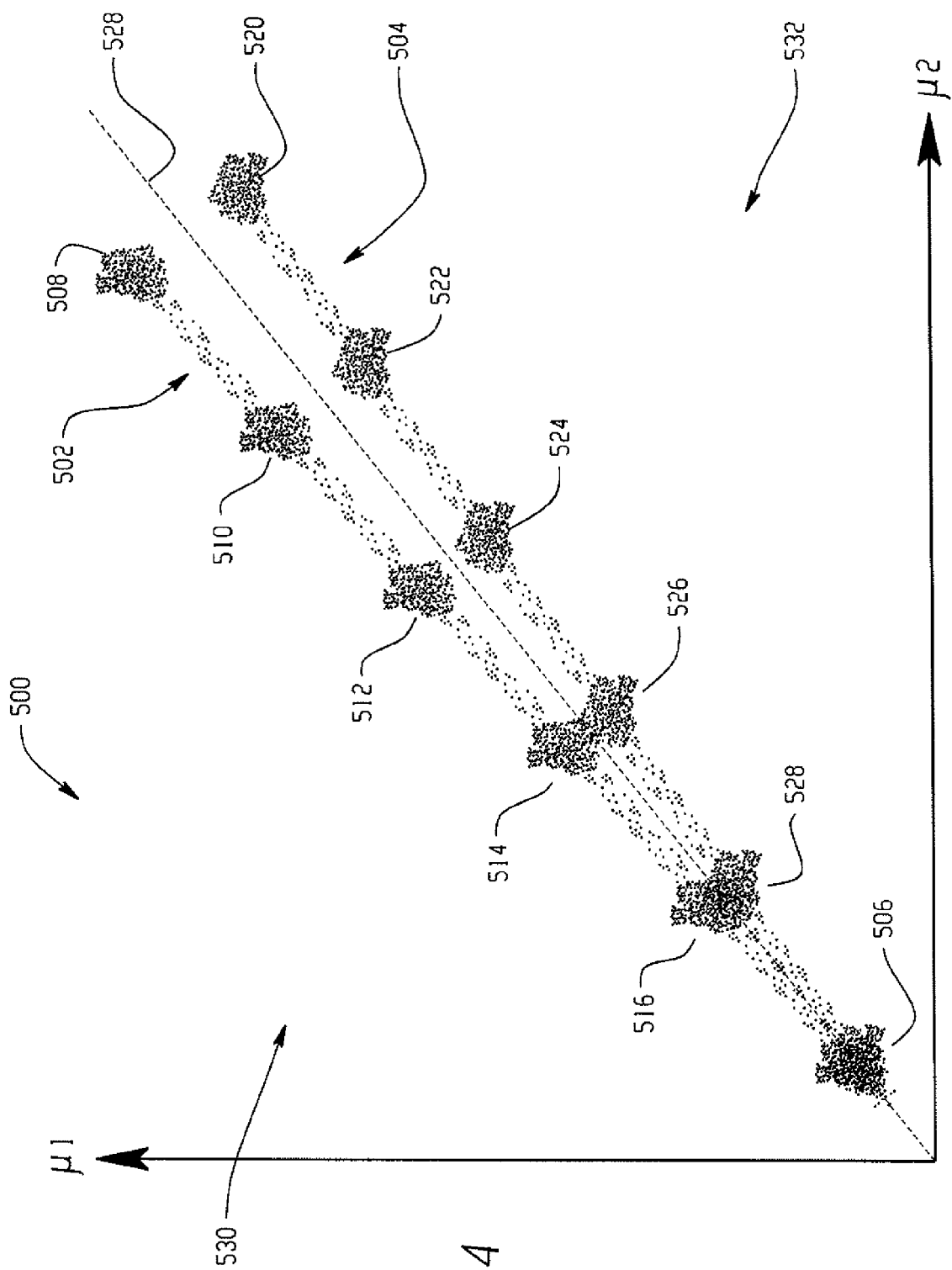
FIG. 4 depicts a two dimensional attenuation space.

With reference to FIGS. 2 and 4, each location x,y,z in the corrected volumetric data 52$_1$ and 52$_2$ is, at step 36, mapped into an attenuation space 500 as a function of the respective attenuation values $\mu 1_{x,y,z}$ and $\mu 2_{x,y,z}$. If a location in image space 52 has a first attenuation value $\mu 1_{x,y,z}$=V1 and a second attenuation value $\mu 2_{x,y,z}$=V2, then the count or value C of the corresponding location in the attenuation space is incremented:

$$C(V1,V2)=C(V1,V2)+1 \qquad \text{Eq. 7}$$

The process is repeated for each location x,y,z in the volume space. The result can be visualized as a two dimensional histogram in attenuation space 500.

By scanning with a known phantom, the relationship between the selected materials and their location in attenuation space 500 can be determined a priori for a particular scanner configuration. In the exemplary case of a dual energy system, each material is located generally along a line 502, 504 in attenuation space 500. Where a material is in a water solution having different concentrations, the different concentrations of the material appear on different locations along the corresponding material line 502, 504, resulting in what looks like "hands-of-a-watch" centered at the attenuation space coordinates of water 506.

FIG. 4 presents schematic results of a simulation (including noise) based on the multiple layer detector and phantom described above.

As can be seen, iodine is located generally along the first line 502, whereas calcium is located generally along the second line 504. The material from cylinder 402 appears generally at location 508, the material from cylinder 404 appears generally at location 510, the material from cylinder 406 appears generally at location 512, and so on. The various cylinders containing calcium appear analogously at locations 520, 522, 524, 526, 528 along the calcium line 504. Pixels or voxels having partial volumes appear along the respective material lines 502, 504.

Returning now to FIG. 2, the material classification function 56 is established at 38. With reference to FIG. 4, an empirical examination of attenuation space 500 yields a material separation line 528 which defines a first material region on one side of the line 530 and a second material region on the other side of the line 532. A location x,y,z in image space 52 having attenuation space coordinates in the first region 530 is classified as iodine; a location having attenuation space 500 coordinates in the second region 532 is classified as calcium.

In a rectangular coordinate system, a simple classification function can be expressed as:

$$M_{x,y,z} = \left(\frac{\mu 1_{x,y,z}}{\mu 2_{x,y,z}}\right) \qquad \text{Eq. 8}$$

Of course, other classification functions and schemes can be implemented. The classification function 56 may return a value $M_{x,y,z}$ indicative not only of the material, but also its concentration and the confidence or probability that the classification is accurate. In the simulation of FIG. 4, for example, the distance from the separation line 528 provides a probability or confidence that the classification is accurate.

It is not necessary for the classification to be binary. Thus, for example, it may be desirable to classify volume space locations which map in the vicinity of the separation line 528 as containing a partial volume or being of an indeterminate material. Volume space locations which map to a region of relatively low concentrations or to a region relatively distant from a material line 502, 504 may similarly be classified as indeterminate.

The material classification function 56 may also be linear function which does not pass through the origin, or a curve or other non-linear function. In another example, the material classification may be implemented as a look up table where the attenuation values provide the coordinates into the table.

When characterized using a suitable phantom, the classification function may also be used to classify more than two materials. When used with a scanner 10 which provides n energy windows or channels, the attenuation space 500 may be modeled as an n-dimensional space, with the classification function 56 established as a function of the location in the n-dimensional space.

The operation of the polychromatic corrector 50 will now be described in greater detail. The polychromatic corrector 50 corrects for beam hardening, which refers to a phenomenon in which relatively lower energies are preferentially attenuated as a polychromatic x-ray beam passes through an object. As the lower energy x-rays are attenuated, the beam becomes progressively harder or more penetrating. The degree of beam hardening is a function of the initial x-ray spectrum, the composition of the material or tissue traversed by the x-ray beam, and the thickness of the material traversed by the x-ray beam.

A deleterious effect of beam hardening is that the location of a particular material in the attenuation space 500 is object dependent. Thus, the accuracy of the material classification function 56 can be improved if this object dependency can be reduced.

The polychromatic correction 50 is applied following reconstruction of the CT data 40 into image space 48 but before the material classification.

Figure 5:
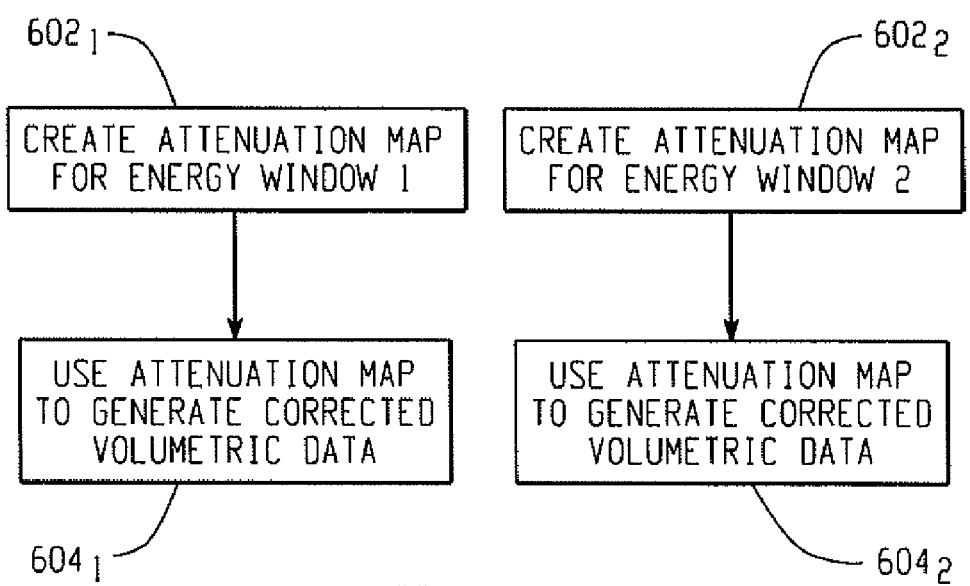
FIG. 5 depicts steps in performing a post-processing polychromatic correction.
Figure 6:
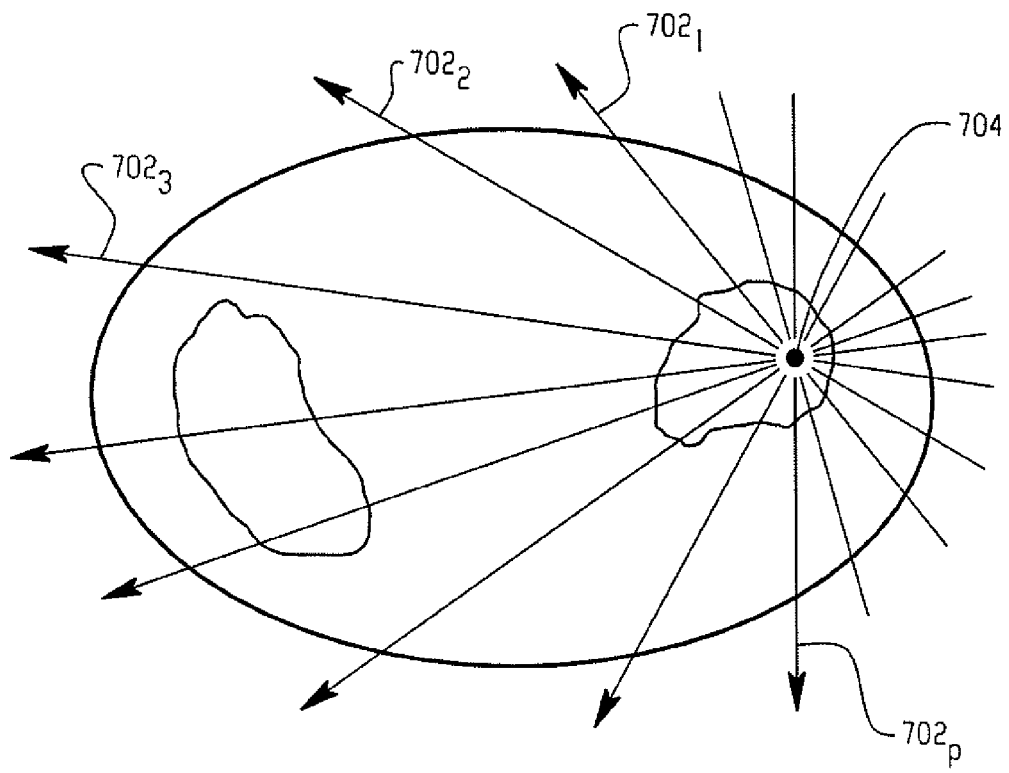
FIG. 6 depicts projections in a volume space.

With reference to FIGS. 5 and 6, an attenuation map is created, at steps 6021, 6022, for each energy spectrum E. As illustrated in FIG. 6 for an arbitrary energy and location 704 in volume space, the attenuation sum along each of plurality p of projections $702_1, 702_2, 702_2 \ldots 702_p$ which pass through the location is calculated. The projections are in turn summed to create an attenuation value $An_{x,y,z}$ for the location in volume space. The process is repeated for each location in volume space and for each energy.

At $604_1, 604_2$, the respective attenuation maps are used to generate the corrected volumetric data $52_1$ and $52_2$ according to the relation:

$$\mu nc_{x,y,z} = (\mu n_{x,y,z} - \mu_0)(1 + F \times A_{x,y,z}) + \mu_0 \qquad \text{Eq. 9}$$

where $\mu nc_{x,y,z}$ is the corrected attenuation value, F is an empirically derived constant that gives the average optimal correction for the relevant set of materials (e.g., iodine and calcium), and $\mu_0$ is the attenuation of water. The empirical factor F can be derived from the resultant images of several different phantoms having different amounts of beam hardening effect. Of course, other correction functions can be used.

Note that the above equation does not change the attenuation of water. Moreover, the corrected attenuation values do not represent the actual or true attenuation in volume space, but rather provide a correction for more accurately mapping the location into attenuation space 500, such that the classification regions will be preserved.

In addition, Eq. 9 assumes that the field of view of the reconstructed data set encompasses the entire object. Where the reconstructed field of view is smaller than the object, another data set which encompasses the entire object is reconstructed. This image set can be reconstructed with a relatively lower resolution and matrix size, as the required attenuation map does not include high spatial frequencies. Once the attenuation map has been created from the low resolution images, the attenuation map can be rescaled to fit the field of view of the original images.

The correction of Eq. 9 is applied separately to each of the two volume spaces $48_1$ and $48_2$. The factor F can be different for each volume space.

Figure 7:
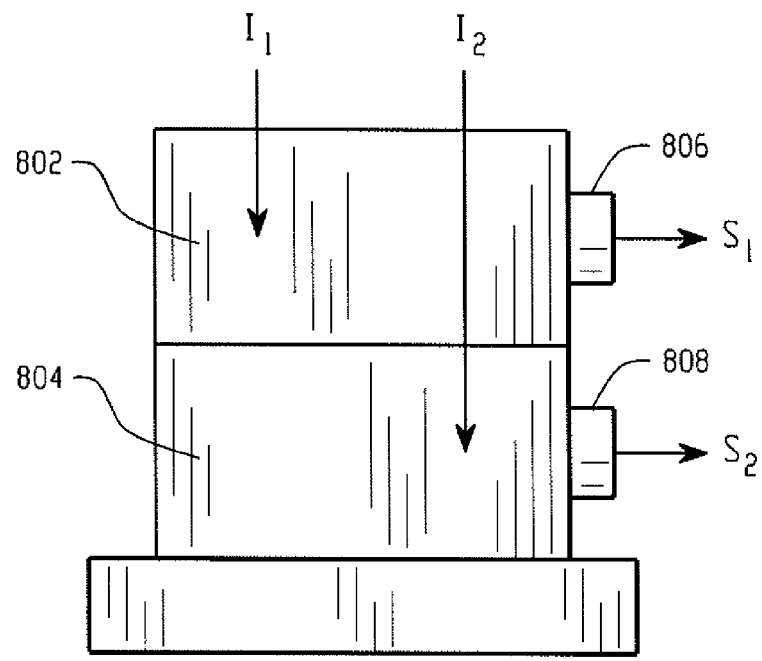
FIG. 7 depicts a dual layer CT detector.

The operation of the energy combiner 42 will now be described in greater detail in connection with a CT detector element having two scintillator layers 802, 804 and corresponding photodetectors 806, 808 as depicted in FIG. 7. $I_1$ and $I_2$ represent the x-ray photon numbers absorbed in the first 802 and second 804 layers, respectively. $S_1$ and $S_2$ represent the raw signals following optics and electronics.

In standard CT the energy dependent equation for the x-ray attenuation is:

$$I = \int dE \cdot I_0(E) \cdot e^{-\int \mu(x,E) dx} \qquad \text{Eq. 10}$$

where I is the absorbed photon number in the detector and $I_0$ is the photon number for an air scan.

Practically, in a standard CT the energy-independent attenuation line integral is calculated by the approximation:

$$\int \mu(x) dx = -\ln \frac{S}{S_0} = -\ln \frac{C \int I(E) E dE}{C \int I_0(E) E dE} \qquad \text{Eq. 11}$$

where S and $S_0$ are the signals through object and air respectively, and C is a conversion factor. The term E inside the integrals is due to the scintillation process.

For the double layer-configuration:

$$I(E) = I_1(E) + I_2(E) \qquad \text{Eq. 12}$$

$$I_0(E) = I_{01}(E) + I_{02}(E) \qquad \text{Eq. 13}$$

where $I_{01}$ and $I_{02}$ are the photon numbers for an air scan, $I_1$ and $I_2$ are the photon numbers for the scan of an object, and I and $I_0$ are the total photon numbers as in standard CT.

The signals are related to the photon numbers by:

$$S_1 = C_1 \int I_1(E) E dE; \; S_2 = C_2 \int I_2(E) E dE \qquad \text{Eq. 14}$$

$$S_{01} = C_1 \int I_{01}(E) E dE; \; S_{02} = C_2 \int I_{02}(E) E dE \qquad \text{Eq. 15}$$

where $C_1$ and $C_2$ are conversion factors specific to each detector type and element.

The attenuation line integral can be calculated by:

$$-\ln \frac{\int I_1(E) E dE + \int I_2(E) E dE}{\int I_{01}(E) E dE + \int I_{02}(E) E dE} = -\ln \frac{S_1 + S_2 \cdot (C_1/C_2)}{S_{01} + S_{02} \cdot (C_1/C_2)} \qquad \text{Eq. 16}$$

Suppose we can directly measure the relation:

$$\frac{\int I_{02}(E) E dE}{\int I_{01}(E) E dE} = k \qquad \text{Eq. 17}$$

This relation depends on the geometry and the materials of the specific system (see below).

The relation between the conversion factors becomes:

$$\frac{C_1}{C_2} = \frac{S_{01}}{S_{02}} \cdot k \qquad \text{Eq. 18}$$

and the attenuation line integral becomes:

$$\int \mu(x)dx = -\ln \frac{(S_1/S_{01}) + (S_2/S_{02}) \cdot k}{1+k} \qquad \text{Eq. 19}$$

In this form, the approximation for calculating the attenuation line integral is the same as in standard CT.

To measure the calibration parameter in air, the relation:

$$\frac{\int I_{02}(E)EdE}{\int I_{01}(E)EdE} = k \qquad \text{Eq. 20}$$

can be measured with a test system of standard single scintillation layer and additional removable appropriate filter which is identical to the upper scintillation layer of the dual energy system. Since the two measurements are done with exactly the same detector:

$$k = \frac{S_{0f}}{S_{0t} - S_{0f}} = \frac{C \int I_{02}(E)EdE}{C \int (I_{0t}(E) - I_{02}(E))EdE} = \frac{\int I_{02}(E)EdE}{\int I_{01}(E)EdE} \qquad \text{Eq. 21}$$

where $S_{0f}$ and $S_{0t}$ are the signals with filter and without filter respectively. The measurement should be done for each pixel.

In principle, this measurement can be done only once and can be used for all double-layer systems with the same configuration.

As noted above, the present technique can also be used with semiconductor or other photon counting detectors. Such detectors can be used to count the number of detected photons and the energy of each photon up to some finite energy resolution. One option for using such detectors in CT is to use a dedicated hardware or channel which counts the number of detected photons without regard to energy. In parallel, the energies of the detected photons are integrated or summed over a known time period. The resultant data streams can be separately reconstructed to provide first and second volumetric data sets. The first data set provides attenuation information based on the number of detected photons, while the second provides attenuation information based on the integral of the energies of the detected photons. These data sets can be used to perform material classification as described above.

The various functions and operations described herein are preferably implemented by way of one or more suitable computers or processors and instructions stored in computer readable memory. When executed, these instructions cause the computer or processor(s) to carry out the described functions.

The invention has been described with reference to the preferred embodiments. Of course, modifications and alterations will occur to others upon reading and understanding the preceding description. It is intended that the invention be construed as including all such modifications and alterations insofar as they come within the scope of the appended claims or the equivalents thereof.

The invention claimed is:

1. A method comprising:
receiving first reconstructed image data indicative of the radiation attenuation of a location in a volume space at a first energy spectrum;
receiving second reconstructed image data indicative of the radiation attenuation of the location in the volume space at a second energy spectrum;
performing a first polychromatic correction based on the radiation attenuations of a plurality of locations in the volume space at the first energy spectrum, wherein the polychromatic correction generates a first corrected radiation attenuation of the location in the volume space at the first energy spectrum;
determining a material composition of the location in the volume space as a function of its location in an attenuation space;
repeating the step receiving first data, receiving second data, and classifying for a plurality of locations; and
generating an image indicative of the material composition.

2. The method of claim 1 further including:
performing a second polychromatic correction based on the radiation attenuations of a plurality of locations in the volume space at the second energy spectrum, wherein the polychromatic correction generates a second corrected radiation attenuation of the location in the volume space at the second energy spectrum;
wherein the step of receiving first data includes receiving the first corrected radiation attenuation and the step of receiving second data includes receiving the second corrected radiation attenuation.

3. The method of claim 2 wherein the step of performing a first polychromatic correction includes generating a first attenuation map and the step of performing a second polychromatic correction includes generating a second attenuation map.

4. The method of claim 1 wherein the step of determining includes classifying the location as containing one of at least first and second materials.

5. The method of claim 4 wherein the second material is a mixture of materials.

6. The method of claim 4 wherein the second material is an indeterminate material.

7. The method of claim 6 wherein the method includes classifying the location as containing one of at least bone and contrast material.

8. The method of claim 1 wherein the step of generating an image includes generating image data for a plurality of locations in the volume space according to the function $P_l = f(\mu_l, M_l)$ where the P is the image data, $\mu$ is a radiation attenuation, M is the material composition, and l is the location in the volume space.

9. The method of claim 8 wherein the radiation attenuation $\mu$ is a composite of the radiation attenuation at the first energy spectrum and the radiation attenuation at the second energy spectrum.

10. The method of claim 1 wherein the step of generating includes generating an image which includes the radiation attenuation of a plurality of locations in the volume space with the material composition superimposed thereon.

11. The method of claim 1 further including:
receiving computed tomography scan data indicative of the radiation attenuation along a plurality of projections through an object at the first energy spectrum;
receiving computed tomography scan data indicative of the radiation attenuation along a plurality of projections through the object at the second energy spectrum;
reconstructing the scan data from the first energy to generate data indicative of the radiation attenuation of the object at a plurality of locations in the volume space at the first energy spectrum;
reconstructing the scan data from the second energy to generate data indicative of the radiation attenuation of the object at a plurality of locations in the volume space at the second energy spectrum.

12. The method of claim 1 wherein the step of determining includes determining the material composition according to the function $M_l = f(\mu 1_l, \mu 2_l)$, where M is the material composition, $\mu 1$ is the radiation attenuation at the first energy spectrum, $\mu 2$ is the radiation attenuation at the second energy spectrum, and l is the location in the volume space.

13. The method of claim 1 wherein the volume space is two dimensional.

14. The method of claim 1 wherein the first and second energy spectra overlap.

15. An apparatus comprising:
means for receiving, for each of a plurality of locations in a volume space, first and second reconstructed image data indicative of the radiation attenuation of the location at respective first and second energy spectra;
means for performing a polychromatic correction on the plurality of locations in the volume space to generate a corrected radiation attenuation at the respective first and second energy spectra and using the corrected radiation attenuation to classify the plurality of locations;
means for determining a material composition of the plurality of locations in the volume space as a function of their respective locations in an attenuation space; and
means for generating an image indicative of the material composition.

16. A method comprising:
classifying a plurality of locations in a computed tomography image space, according to a material classification function $M_l = f(\mu 1_l, \mu 2_l \ldots \mu n_l)$, where M is a material, n is the number of energy spectra, $\mu n$ is a radiation attenuation at energy spectrum n, and l is a location in the image space, and wherein n is greater than or equal to 2;
performing a polychromatic correction on the plurality of locations in the image space to generate a corrected radiation attenuation at each energy spectrum and using the corrected radiation attenuation to classify the plurality of locations; and
presenting a result of the classification in human readable form.

17. The method of claim 16 wherein the step of classifying a plurality of locations in the computed tomography image space includes classifying each location in the image space as a function of its location in an n-dimensional attenuation space.

18. The method of claim 16 wherein performing a polychromatic correction includes generating an attenuation map for each energy spectrum n.

19. The method of claim 16 wherein n equals 2.

20. The method of claim 16 wherein presenting a result of the classification includes generating image data for the plurality of locations according to the function $P_l = f(\mu_l, M_l)$, where the P is the image data and $\mu$ is a radiation attenuation.

21. The method of claim 20 wherein the radiation attenuation is a composite of the radiation attenuation at a plurality of energy spectra.

22. The method of claim 21 including generating an image which includes the radiation attenuation with the results of the classification superimposed thereon.

23. The method of claim 16 wherein the classification function is a linear function.

24. The method of claim 16 where $\mu 1$ is an attenuation based on a count of detected photons and $\mu 2$ is an attenuation based on an integral of the energies of detected photons.

* * * * *